United States Patent [19]
Heine et al.

[11] Patent Number: 5,196,964
[45] Date of Patent: Mar. 23, 1993

[54] MAGNIFIER

[75] Inventors: Helmut A. Heine; Otto H. Schmidt, both of Herrsching; Helmut Rosenbusch, Welthelm, all of Fed. Rep. of Germany

[73] Assignees: Heine Optotechnik GmbH & Co. KG, Herrsching, Fed. Rep. of Germany; Propper Manufacturing Co., Inc., Long Island City, N.Y.

[21] Appl. No.: 637,908

[22] Filed: Jan. 7, 1991

[30] Foreign Application Priority Data

Jan. 9, 1990 [DE] Fed. Rep. of Germany ... 9000190[U]

[51] Int. Cl.⁵ .............................................. G02B 27/02
[52] U.S. Cl. .................................... 359/800; 359/803; 359/812; 362/109; 362/157
[58] Field of Search ............ 359/800, 802, 798, 803, 359/808, 809, 810, 811, 812, 815, 817; 362/109, 157, 268, 311, 368

[56] References Cited

U.S. PATENT DOCUMENTS

| | | | |
|---|---|---|---|
| 1,145,959 | 7/1915 | Amstutz | 359/817 |
| 1,396,607 | 11/1921 | Post | 359/798 |
| 1,804,105 | 5/1931 | Martens | 359/800 |
| 2,087,081 | 7/1937 | Bock | 359/800 |
| 4,205,747 | 6/1980 | Gilliam et al. | 359/808 |
| 4,225,907 | 9/1980 | Erdell | 359/803 |
| 4,681,413 | 7/1987 | Schmidt et al. | 351/205 |
| 4,684,227 | 8/1987 | Schmidt et al. | 351/205 |
| 4,859,032 | 8/1989 | Feinbloom | 359/802 |

Primary Examiner—Loha Ben
Attorney, Agent, or Firm—Blum Kaplan

[57] ABSTRACT

A magnifier for observing a surface includes a housing, a detachable window attachment coupled to a first end of the housing and an eyepiece coupled to a second end of the housing. A light source attachment is coupled to the housing for supplying light to the hollow interior of the housing. The light source attachment and housing each have major axes which extend in different directions and form an angle between approximately 110° and 120°. Photoconductive material serves as a light guide for directing the light from the light source attachment to the window attachment.

40 Claims, 4 Drawing Sheets

MAGNIFIER

BACKGROUND OF THE INVENTION

This invention relates to a magnifier, and in particular, to a magnifier for use in, but not limited to, the field of dermatology where minute areas are to be examined.

Occasionally or on a more frequent basis, the need to examine a surface with a high degree of accuracy can arise in the daily course of events and is especially common in the fields of technology and medicine. In the field of dermatology, there exists an ever increasing demand for a magnifier which provides a highly accurate view of minute areas of skin. Early recognition of pathologic changes commonly results from a detailed examination of such minute areas of skin.

Conventional manual or placement magnifiers cannot be easily handled and shade areas to be examined. Reflections can result which interfere with and prevent a thorough examination of the skin.

Accordingly, it is desirable to provide a magnifier which can be more easily handled. The area under examination also should not be shaded by the magnifier. The magnifier should therefore avoid producing interfering reflections so that a highly accurate view of a minute area of skin can be observed.

SUMMARY OF THE INVENTION

Generally speaking, in accordance with the invention, a magnifier for observing a surface includes a housing having a first end and a second end and a hollow interior. A window attachment is coupled to the first end of the housing for observing the surface therethrough. An eyepiece is coupled to the second end of the housing for magnifying the surface observed through the window. A light source attachment is coupled to the housing for supplying light to the hollow interior of the housing. The light source attachment includes a handle for controlling the position of the magnifier relative to the surface.

By supplying light to the hollow interior of the housing, the light can be directed through the window for illuminating the surface to be observed without shading areas of the surface to be examined. The handle of the light source attachment permits the magnifier to be simply and easily controlled in positioning the latter relative to the surface to be examined.

The handle includes a power source such as, but not limited to, one or more batteries, for supplying power to the light source. An inlet of the housing permits luminous communication between the light source and the interior of the housing.

Preferably, the window attachment is operable for placement on the surface to be examined. The housing and light source attachment each include major axes extending in different directions so as to form an obtuse angle between these major axes. Preferably, this obtuse angle ranges between approximately 110° to 120°.

In one feature of the invention both the housing and light source attachment are tubular. In another feature of the invention a transparent disk serves as the window in the window attachment. Alternatively, a cylindrical casing filled with transparent material serves as the window for observing relatively minute areas.

The window attachment includes an exterior wall having at least one slot or groove extending therethrough. The housing includes at least one protrusion extending inwardly. Each slot of the exterior wall is operable for slidably receiving a corresponding protrusion to secure the window to the housing and for slidably releasing the corresponding protrusion to separate the window from the housing.

The housing also includes a light stop disposed within the hollow interior of the housing for blocking light from travelling toward the eyepiece other than light which has passed through the window. The light stop is disposed between the inlet and the eyepiece.

In another feature of the invention, a light guide is provided which includes a first portion and a second portion which are connected to one another. The first portion of the light guide extends within the light source attachment. The second portion of the light guide is approximately circular and disposed within the hollow interior of the housing. Preferably, the second portion is substantially in the shape of a ring.

In yet another feature of the invention the window includes a scale disposed thereon for measuring the surface under observation. In still another feature of the invention the window includes a color filter.

Accordingly, it is an object of the invention to provide an improved magnifier which can be easily handled.

It is another object of the invention to provide an improved magnifier which does not shade portions of the surface under observation.

It is a further object of the invention to provide a magnifier which avoids producing interfering reflections so that a highly accurate view of a minute area of skin can be observed.

Still other objects and advantages of the invention will, in part, be obvious and will, in part, be apparent from the specification.

The invention accordingly comprises the several steps and relation of one or more of such steps with respect to each of the others, and the apparatus embodying features of construction, a combination of elements and arrangements of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 4b is a cross-sectional view of the light conductive along lines 4b—4b of FIG. 4a;

DETAILED DESCRIPTION OF THE PREFERRED EMBODIMENTS

Figure 1:
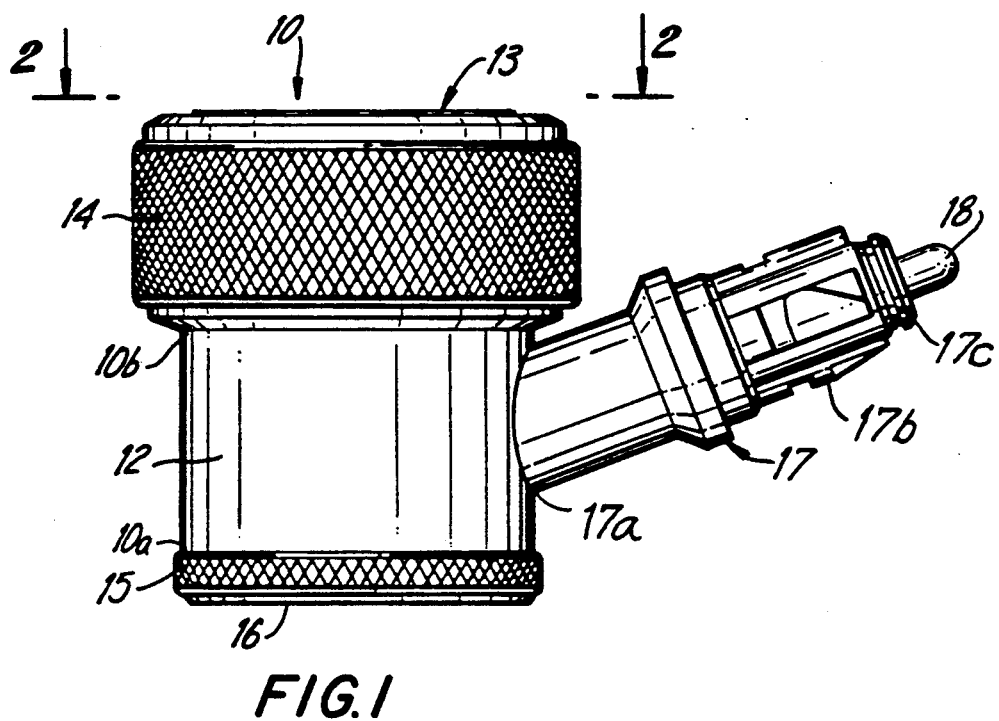
FIG. 1 is a side elevational view of a magnifier in accordance with a first embodiment of the invention.
Figure 2:
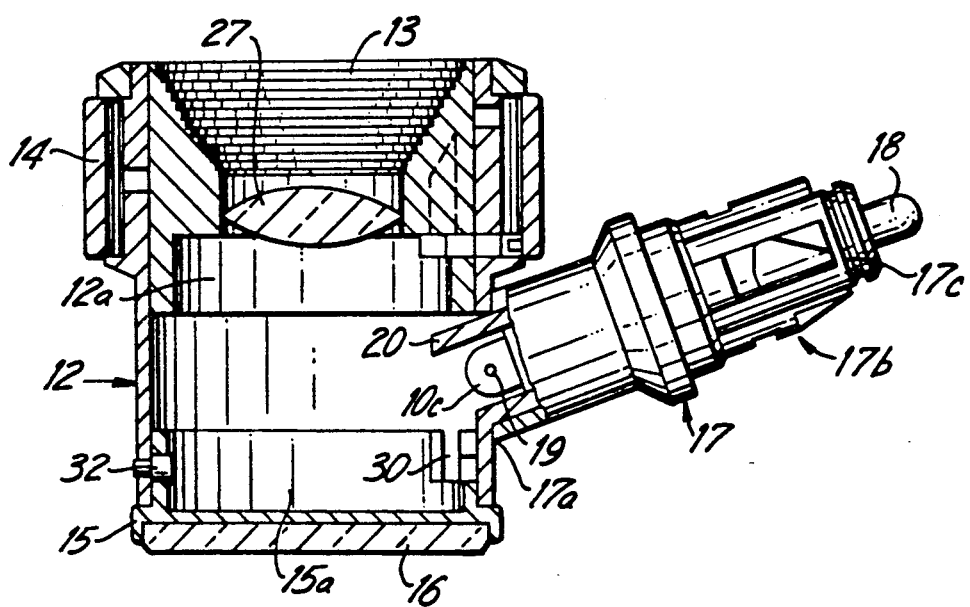
FIG. 2 is a cross-sectional view of the magnifier taken along lines 2—2 of FIG. 1.
Figure 7:
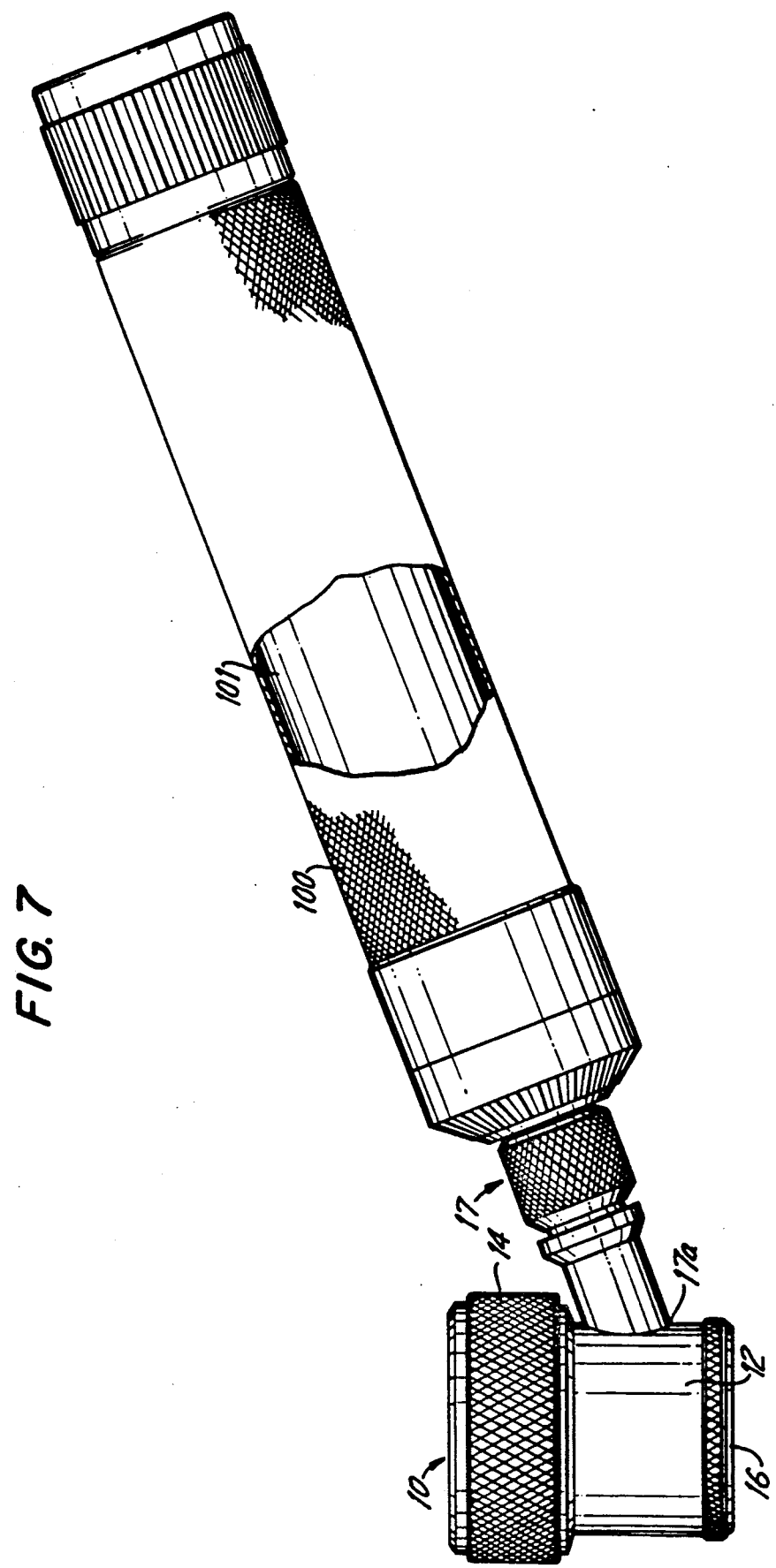
FIG. 7 is a side elevation view of the magnifier of FIG. with a handle attached thereto.

Reference is first made to FIGS. 1 and 2 of the drawings which depict a magnifier, generally indicated at 10 and constructed in accordance with a first preferred embodiment of the invention. Magnifier 10 includes a tubular case 12 having a hollow interior 12a. At a distal end 10a, tubular case 12 is provided with a window attachment 15 suitable for contact with a surface to be examined. At a proximal end 10b, tubular case 12 includes an tubular case 12 is covered by an attachment 17. As shown in FIG. 7, attachment 17, which is coupled at a proximal end 17a to case 12 and preferably integral therewith, includes a power supply handle 100 coupled thereto. Handle 100 includes a rechargeable battery 101.

Attachment 17 also includes a distal end 17b having a substantially circular opening 17c through which a light source 18 is slidably received. A frictional fit between light source 18 and distal end 17b securely positions light source 18 within attachment 17. Light source 18 includes an incandescent bulb 19 for illuminating the hollow interior 12a of case 12. Photoconductor material, as discussed below, can be provided to guide the light from attachment 17 through light inlet 10c into hollow interior 12a of tubular case 12.

The light from light source 18 is introduced through the side of tubular case 12 by attachment 17. Since the light is introduced from the side of case 12 into hollow interior 12a, it is nearly impossible for shading of the light to occur in the area to be examined by the observer. Accordingly, interfering reflections commonly produced by such shading in conventional magnifiers are avoided. Adjustable eyepiece 13 permits proper focusing of the surface to be examined and positioning of lens 27 at various positions by means of a focusing ring 14 to enable the observer to examine the surface at different depths. Adjustable eyepiece 13 is especially important in the field of dermatology in examining minute areas of skin.

Attachment 17 is preferably integrally connected at a slanting angle to tubular case 12 at an angle between approximately 110° to 120°. At angles less than approximately 110° a considerable loss of light results since the smaller angle causes too great a portion of the light to be reflected back toward attachment 17 rather than toward window attachment 15. An angle greater than 120° would make it difficult to couple attachment 17 to tubular case 12. At angles of greater than 120°, attachment 17 would also need to be longer in length which would impair the handling of magnifier 10.

As shown in FIGS. 1, 2, 3, 4a, 4b and 6, a transparent disk 16 can serve as the window for window attachment 15. Alternatively, as shown in FIG. 5, a cylindrical body 25 filled with transparent material can serve as the window for window attachment 15. Disk 16 and cylindrical body 25 are interchangeable. Generally, disk 16 is used to examine relatively large surfaces. Cylindrical body 25 has a smaller diameter than disk 16 for examining relatively smaller surfaces and angled areas. Cylindrical body 25 is typically used in the field of dermatology when the inferior root of the nose or the folds of the skin are to be examined.

As shown in FIG. 2, a light stop 20 is disposed in tubular case 12 above light inlet 10c. Light stop 20 substantially prevents light from traveling directly toward eyepiece 13 from light source 18 which would otherwise adversely impact on the image of the surface under observation. Substantially all light traveling toward eyepiece 13 travels from light source 18 through window attachment 15 to the surface under observation, the image of which is reflected back through window attachment 15 toward eyepiece 13.

Figure 3:
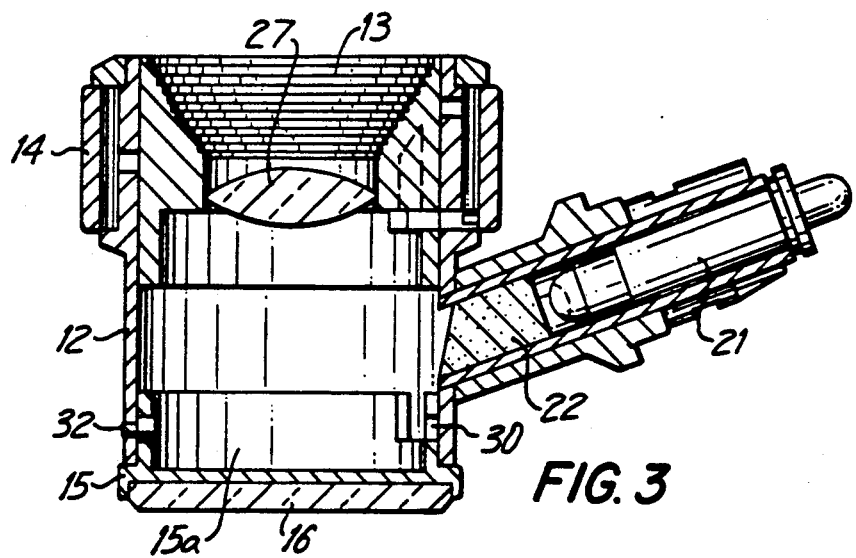
FIG. 3 is a cross-sectional view of a magnifier in accordance with an alternative embodiment of the invention.

Referring now to FIG. 3 of the surface, a lens lamp 21 serves as the source of light for illuminating the surface under observation. Light is directed through a photoconductor 22 serving as a light guide which is inserted into attachment 17 proximate to inlet 10a for directing light toward disk 16.

Figure 4A:
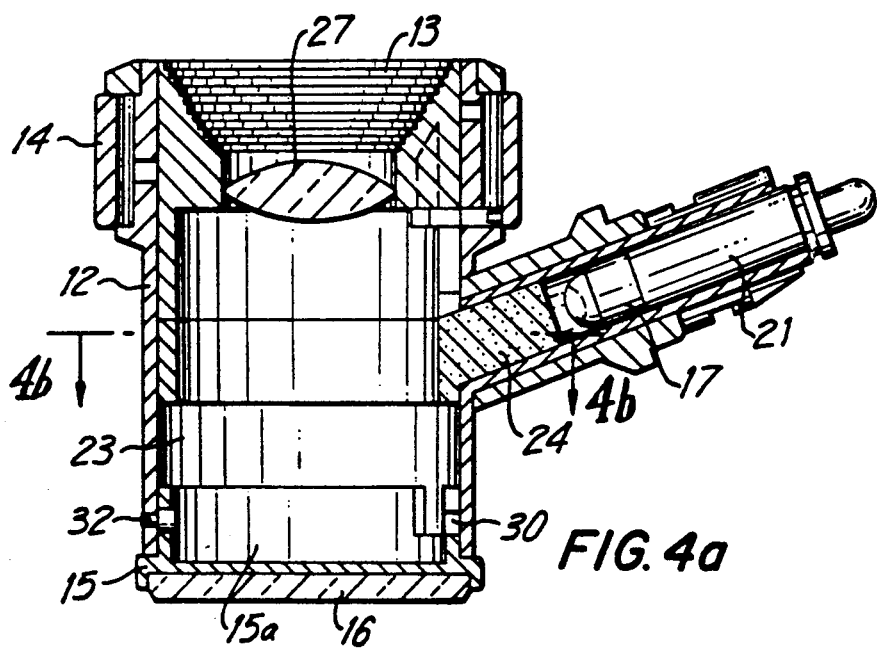
FIG. 4a is a cross-sectional view of a magnifier in accordance with another alternative embodiment of the invention.
Figure 4B:
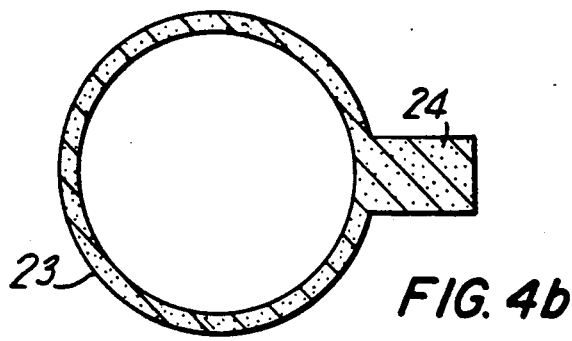
Figure 5:
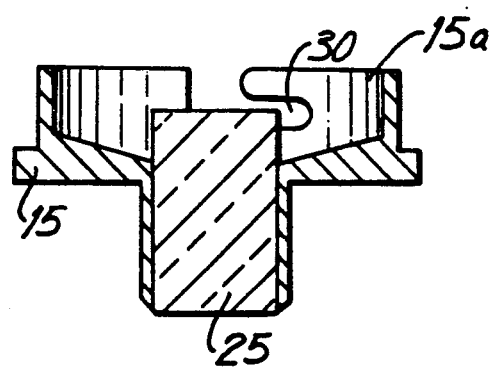
FIG. 5 is a fragmented cross-sectional view of a magnifier in accordance with still another alternative embodiment of the invention.

Alternatively, as shown in FIGS. 4a and 4b, a circular photoconductor 23 in the shape of a ring is disposed proximate to window attachment 15 in hollow interior 12a of tubular case 12. A rod shaped photoconductor 24 is disposed in attachment 17 filling inlet 10c and extending into hollow interior 12a. Photoconductors 23 and 24 are connected together. Light from lamp 21 is guided through photoconductor 24 similar to photoconductor 22. Light is therefore directed toward window attachment 15 by photoconductors 23 and 24.

In both FIGS. 3 and 4a, magnifier 10 operates without a light stop through use of one or more photoconductors to guide the light toward window attachment 15. A high level of luminous intensity is directed to the surface under observation through disk 16. An exceptionally high level of luminous intensity is provided when photoconductor 23 is near window attachment 15 as shown in FIG. 4a. Magnifier 10 therefore provides a glare free device for examination of a surface which is illuminated by a relatively high intensity of light.

As shown in FIGS. 2, 3, 4a and 5, window attachment 15 includes a wall 15a having at least one slot/groove 30. Casing 12 includes for each slot 30 a corresponding protrusion 32 extending inwardly into hollow interior 12a as shown in FIGS. 2, 3 and 4a. This arrangement allows window attachment 15 to be conveniently and quickly detached and connected to casing 12. For example, when the observer needs to switch from a large viewing area to a smaller viewing area, disk 16 can be replaced with cylindrical body 25 as shown in FIG. 5.

Figure 6:
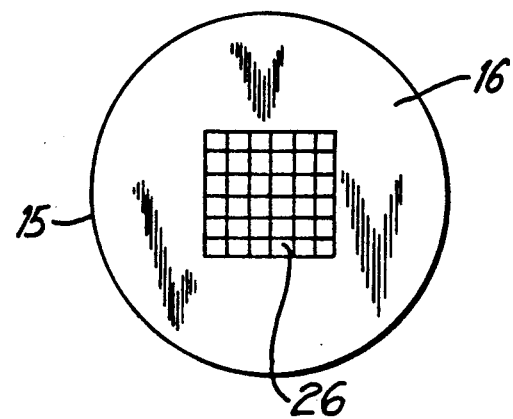
FIG. 6 is a plan view of a contact disk including a measurement grid.

Referring to FIG. 6, measurements of the surface under examination can be made by providing a measurement grid/measurement scale 26. Direct measurement of the surface being examined results. In an alternative embodiment, measurement grid 26 may be detached and turned over to its opposite side so that measurement grid 26 does not directly contact the examined surface. In addition, disk 16 can be constructed with a colored filter to identify particular areas of the surface. In one example, a neutral color filter is used.

In accordance with another alternative embodiment of the invention, a contact liquid may be applied to the surface under examination and/or to the outside surface of window attachment 15 to substantially eliminate the reflective properties between the surface to be examined and disk 16. In accordance with yet another alternative embodiment of the invention, three dimensional viewing is possible. In special examinations, an enlargement of the viewing surface may be conducted. For example, examination of capillaries in a groove of a nail bed can be provided by the invention. In accordance with the invention, video cameras, CCD chips or photographic equipment can be used in combination with magnifier 10.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A magnifier for observing a surface, comprising;
   a housing having a first end and a second end and a hollow interior, said housing including a major axis extending in a first direction;
   window means including a window and coupled to said first end of said housing for observing the surface therethrough;
   eyepiece means coupled to said second end of said housing for magnifying the surface observed through said window means;
   light source means coupled to said housing for supplying light to the hollow interior of said housing, said light source means including a major axis extending in a second direction so that said first direction of said housing and said second direction of said light source means form an obtuse angle ranging between approximately 110° to 120°; and
   coupling means for separating said window means from said housing and securing said window means to said housing.

2. The magnifier of claim 1, wherein said light source means includes handle means for controlling the position of said magnifier relative to said surface.

3. The magnifier of claim 2, wherein said handle means includes power means for supplying power to said light source means.

4. The magnifier of claim 3, wherein said housing includes inlet means for luminous communication between said light source means and the interior of said housing.

5. The magnifier of claim 1, wherein said housing includes inlet means for luminous communication between said light source means and the interior of said housing.

6. The magnifier of claim 5, wherein said housing includes light stop means within the hollow interior of said housing for blocking light from traveling toward said eyepiece means other than light which has passed through said window means.

7. The magnifier of claim 6, wherein said light stop means is displaced between said inlet means and said eyepiece means.

8. The magnifier of claim 1, wherein said window means is operable for placement on said surface.

9. The magnifier of claim 1, wherein said light source means includes a proximal end and distal end, said proximal end being integral with said housing.

10. The magnifier of claim 1, wherein said housing is tubular.

11. The magnifier of claim 1, wherein said window means includes a transparent disk serving as said window.

12. The magnifier of claim 11, wherein said transparent disk includes scale means for measuring the surface under observation.

13. The magnifier of claim 1, wherein said window means includes a cylindrical casing.

14. The magnifier of claim 1, wherein said cylindrical casing is filled with transparent material serving as said window.

15. The magnifier of claim 13, wherein said cylindrical casing is filled with transparent material serving as said window.

16. The magnifier of claim 1, wherein said housing includes light stop means within the hollow interior of said housing for blocking light from traveling toward said eyepiece means other than light which has passed through said window means.

17. The magnifier of claim 1, further including light guide means for guiding said light from said light source means to within the hollow interior of said housing.

18. The magnifier of claim 17, wherein said light guide means includes a first portion extending within said light source means and a second portion being substantially circular and disposed within the hollow interior of said housing.

19. The magnifier of claim 18, wherein said second portion of said light guide means is proximate said window means.

20. The magnifier of claim 19, wherein said second portion is substantially in the shape of a ring.

21. The magnifier of claim 19, wherein the first portion of said light guide means is connected to the second portion of said light guide means.

22. The magnifier of claim 19, wherein said light guide means is a photoconductor.

23. The magnifier of claim 18, wherein said second portion is substantially in the shape of a ring.

24. The magnifier of claim 20, wherein the first portion of said light guide means is connected to the second portion of said light guide means.

25. The magnifier of claim 24, wherein said light guide means is a photoconductor.

26. The magnifier of claim 23, wherein said light guide means is a photoconductor.

27. The magnifier of claim 18, wherein the first portion of said light guide means is connected to the second portion of said light guide means.

28. The magnifier of claim 18, wherein said light guide means is a photoconductor.

29. The magnifier of claim 1, wherein said window means includes scale means disposed on said window for measuring the surface under observation.

30. The magnifier of claim 1, wherein the window means includes a color filter.

31. The magnifier of claim 1, wherein said housing includes light stop means within the hollow interior of said housing for blocking light from traveling toward said eyepiece means other than light which has passed through said window means.

32. The magnifier of claim 1, further including light guide means for guiding said light from said light source means to within the hollow interior of said housing.

33. The magnifier of claim 32, wherein said light guide means includes a first portion extending within said light source means and a second portion being substantially circular and disposed within the hollow interior of said housing.

34. A magnifier for observing a surface, comprising:

a housing having a first end and a second end and a hollow interior;

window means including a window and coupled to said first end of said housing for observing the surface therethrough, said window means including an exterior wall having at least one slot extending therethrough and said housing including at least one protrusion extending inwardly, each said slot operable for slidably receiving a corresponding protrusion to secure said window means to said housing and for slidable releasing the corresponding protrusion to separate said window means from said housing, each said slot and corresponding protrusion serve as a coupling means for separating said window means from said housing and securing said window means to said housing;

eyepiece means coupled to said second end of said housing for magnifying the surface observed through said window means; and light source means coupled to said housing for supplying light to the hollow interior of said housing.

35. A magnifier for observing a surface, comprising:

a housing having a first end and a second end and a hollow interior, said housing including a major axis extending in a first direction;

window means including a transparent disk serving as a window and coupled to said first end of said housing for observing the surface therethrough;

eyepiece means coupled to said second end of said housing for magnifying the surface observed through said window means; and light source means coupled to said housing for supplying light to the hollow interior of said housing, said light source means including a major axis extending in a second direction so that said first direction of said housing and said second direction of said light source means form an obtuse angle ranging between approximately 110° to 120°.

36. A method of assembling a magnifier comprising the steps of:

coupling window means to a first end of a housing having a hollow interior;

coupling magnifying eyepiece means to a second end of the housing; and connecting light source means to an inlet of said housing to provide luminous communication between the hollow interior of said housing and said light source means;

wherein said light source means includes a first major axis and said housing includes a second major axis and wherein the step of connecting said light source to said inlet forms an obtuse angle between the first and second major axes ranging between approximately 110° to 120°.

37. The method of claim 36, further including providing light stop means within the hollow interior of said housing for blocking light traveling from said light source means toward said eyepiece means other than light which has passed through said window means.

38. The method of claim 36, further including providing photoconductor means from said light source means to the hollow interior of said housing.

39. A method of assembling a magnifier comprising the steps of:

coupling window means to a first end of a housing having a hollow interior;

coupling magnifying eyepiece means to a second end of the housing;

connecting light source means to an inlet of said housing to provide luminous communication between the hollow interior of said housing and said light source means; and blocking light traveling from said light source means toward said eyepiece means other than light which has passed through said window means by means of a light stop within the hollow interior of said housing.

40. A method of assembling a magnifier comprising the steps of:

coupling window means to a first end of a housing having a hollow interior;

coupling magnifying eyepiece means to a second end of the housing;

connecting light source means to an inlet of said housing to provide luminous communication between the hollow interior of said housing and said light source means; and providing photoconductor means in the hollow interior of said housing to direct light from said light source means to the hollow interior of said housing.

* * * * *